US006981522B2

(12) United States Patent
O'Connor et al.

(10) Patent No.: US 6,981,522 B2
(45) Date of Patent: Jan. 3, 2006

(54) MICROFLUIDIC DEVICES WITH DISTRIBUTING INPUTS

(75) Inventors: Stephen D. O'Connor, Pasadena, CA (US); Christoph D. Karp, Pasadena, CA (US); Eugene Dantsker, Sierra Madre, CA (US)

(73) Assignee: Nanostream, Inc., Pasadena, CA (US)

( * ) Notice: Subject to any disclaimer, the term of this patent is extended or adjusted under 35 U.S.C. 154(b) by 397 days.

(21) Appl. No.: 10/160,393

(22) Filed: May 30, 2002

(65) Prior Publication Data

US 2002/0185183 A1 Dec. 12, 2002

Related U.S. Application Data

(60) Provisional application No. 60/296,897, filed on Jun. 7, 2001, and provisional application No. 60/357,683, filed on Feb. 13, 2002.

(51) Int. Cl.
*F15C 1/06* (2006.01)
*F16K 37/00* (2006.01)

(52) U.S. Cl. .................. 137/803; 137/833; 137/828; 137/559; 204/601

(58) Field of Classification Search ............. 137/833, 137/803, 828, 559; 204/601
See application file for complete search history.

(56) References Cited

U.S. PATENT DOCUMENTS

| 3,587,615 A | 6/1971 | Thomson | 137/81.5 |
| 3,680,576 A | 8/1972 | Kiwak | 137/81.5 |

(Continued)

FOREIGN PATENT DOCUMENTS

| EP | 1 106 244 A2 | 6/2001 |
| EP | 1 123 734 A2 | 8/2001 |

(Continued)

OTHER PUBLICATIONS

Kikutani, Y., et al., "Fabrication of a Glass Microchip with a Three–Dimensional Channel Network and its Application to a Single–Chip Combinatorial Synthetic Reactor," *Micro Total Analysis Systems*, J.M. Ramsey and A. van den Berg (eds.), Kluwer Academic Publishers, The Netherlands, 2001, pp. 161–162.

Sato, Kiichi, et al., "Integrated Immunoassay System Using Multichannel Microchip for Simultaneous Determination," *Micro Total Analysis Systems*, J.M. Ramsey and A. van den Berg (eds.), Kluwer Academic Publishers, The Netherlands, 2001, pp. 511–512.

(Continued)

*Primary Examiner*—A. Michael Chambers

(74) *Attorney, Agent, or Firm*—Vincent K. Gustafson; Intellectual Property/Technology Law

(57) ABSTRACT

Microfluidic devices having a plurality of functional features for performing one or more fluidic operations in parallel are provided. Reagents, samples or other fluids common to multiple functional features ("common fluids") may be input into a microfluidic device or system through one or more distributing inputs that divide and distribute the common fluids as desired. The use of a multi-layer fabrication technique allows multiple distributing inputs to distribute to multiple functional features in a microfluidic device without undesirable fluid channel intersections.

36 Claims, 14 Drawing Sheets

U.S. PATENT DOCUMENTS

| | | | |
|---|---|---|---|
| 4,952,266 A | 8/1990 | Tsuruta et al. | 156/243 |
| 5,250,263 A | 10/1993 | Manz | 422/81 |
| 5,534,328 A | 7/1996 | Ashmead et al. | 428/166 |
| 5,690,763 A | 11/1997 | Ashmead et al. | 156/60 |
| 5,727,618 A | 3/1998 | Mundinger et al. | 165/80.4 |
| 5,744,366 A | 4/1998 | Kricka et al. | 436/63 |
| 5,846,396 A | 12/1998 | Zanzucchi et al. | 204/601 |
| 5,863,502 A | 1/1999 | Southgate et al. | 422/58 |
| 5,869,004 A | 2/1999 | Parce et al. | 422/100 |
| 5,885,470 A | 3/1999 | Parce et al. | 216/33 |
| 6,033,544 A | 3/2000 | Demers et al. | 204/450 |
| 6,074,725 A | 6/2000 | Kennedy | 428/188 |
| 6,103,199 A | 8/2000 | Bjornson et al. | 422/100 |
| 6,123,316 A | 9/2000 | Biegelsen et al. | 251/129.01 |
| 6,167,910 B1 | 1/2001 | Chow | 137/827 |
| 6,221,654 B1 | 4/2001 | Quake et al. | 435/287.3 |
| 6,258,263 B1 | 7/2001 | Henderson et al. | 210/198.2 |
| 6,293,012 B1 | 9/2001 | Moles | 29/890.124 |
| 6,352,577 B1 | 3/2002 | Martin et al. | 96/4 |
| 6,418,968 B1 * | 7/2002 | Pezzuto et al. | 137/833 |
| 6,444,461 B1 | 9/2002 | Knapp et al. | 435/283.1 |
| 6,494,614 B1 | 12/2002 | Bennett et al. | 366/336 |
| 6,499,499 B2 * | 12/2002 | Dantsker et al. | 137/1 |
| 6,623,860 B2 | 9/2003 | Hu et al. | 428/411.1 |
| 6,645,432 B1 | 11/2003 | Anderson et al. | 422/100 |
| 2002/0037499 A1 | 3/2002 | Quake et al. | 435/5 |
| 2002/0048536 A1 | 4/2002 | Bergh et al. | 422/130 |

FOREIGN PATENT DOCUMENTS

| | | |
|---|---|---|
| WO | WO 96/15576 | 5/1996 |
| WO | WO 99/15888 | 4/1999 |
| WO | WO 99/19717 | 4/1999 |
| WO | WO 99/29497 | 6/1999 |
| WO | WO 99/33559 | 7/1999 |
| WO | WO 99/48599 | 9/1999 |
| WO | WO 99/60397 | 11/1999 |
| WO | WO 00/21659 | 4/2000 |

OTHER PUBLICATIONS

Peters, Ralf–Peter, "Disposable BioMEMS: From Development to Mass Production," BioMEMS & Biomedical Nanotechnology World 2000, Sep. 23–26, 2000, Hyatt Regency Columbus, Columbus, Ohio, Sunday, Sep. 24.

Martin, P.M., et al., *Fabrication of plastic microfluidic components*, "Microfluidic Devices and Systems," SPIE, vol. 3515, Sep. 21–22, 1998, Santa Clara, California, pp. 172–176.

Ehrfeld W. et al., "Potentials and Realization of Microreactors," DECHEMA Monographs vol. 132–VCH Verlagsgesellschaft 1996.

* cited by examiner

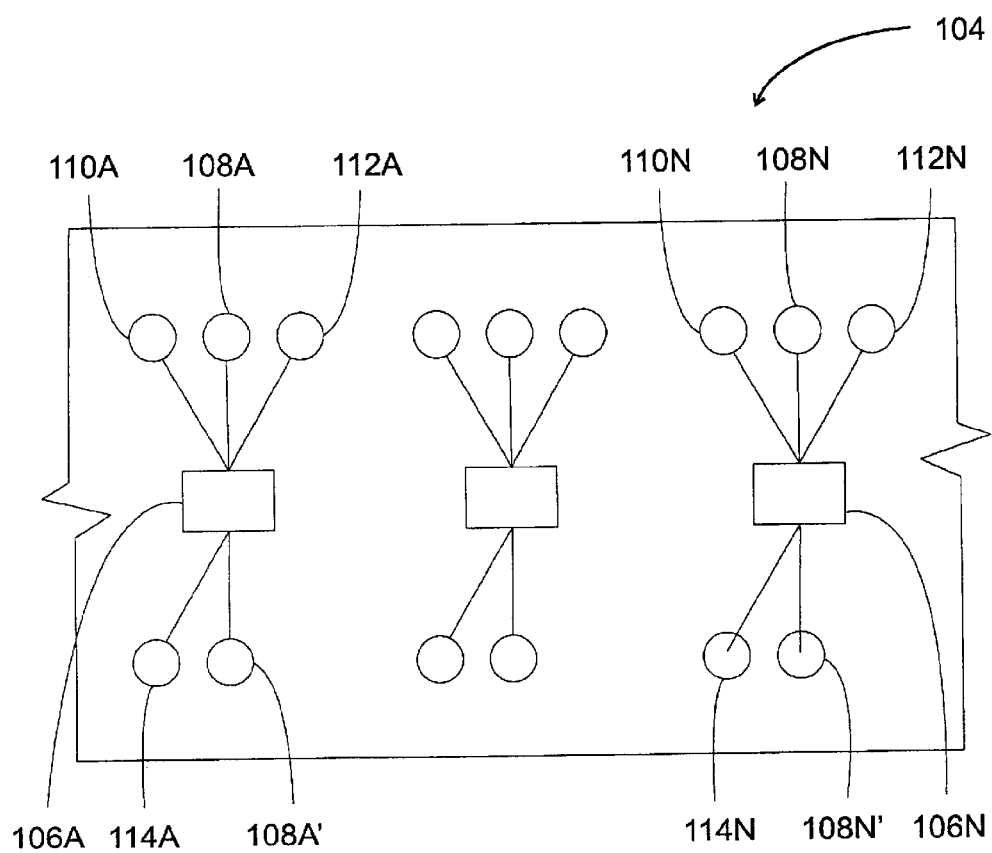
FIG._ 2A

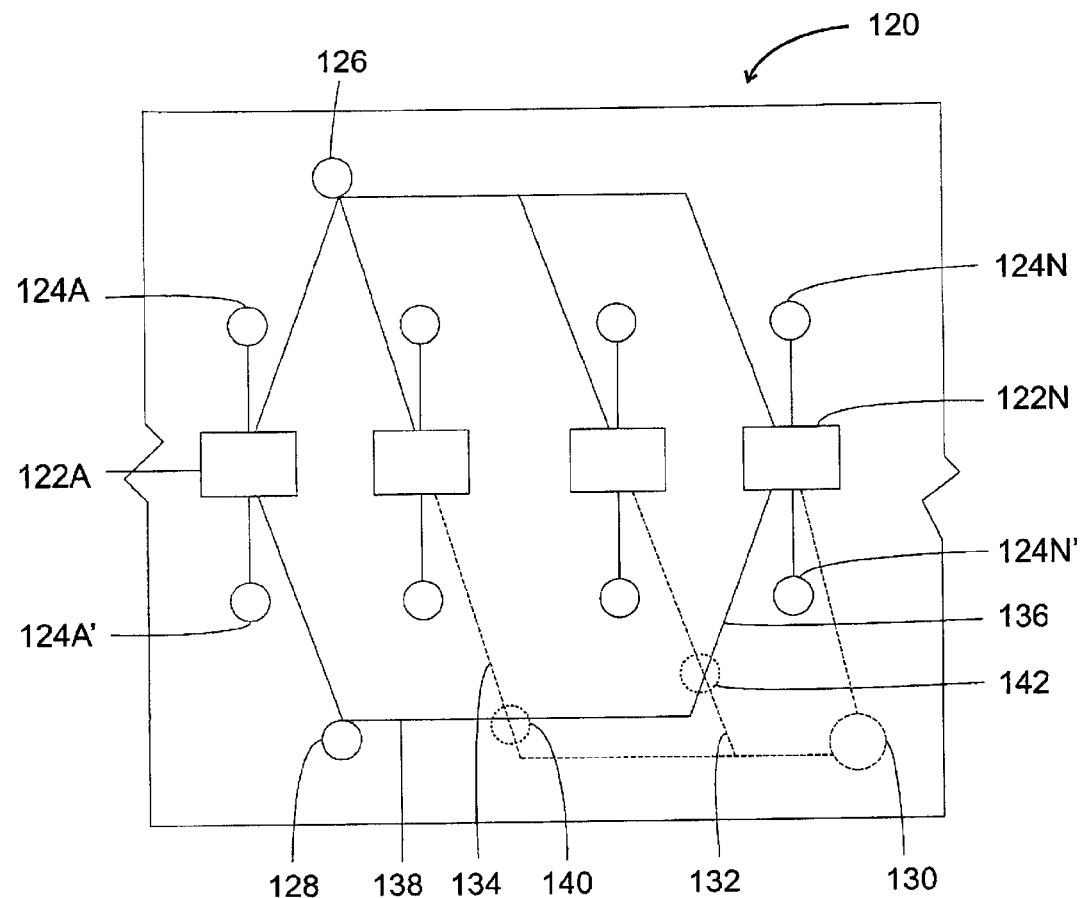
FIG._ 2B

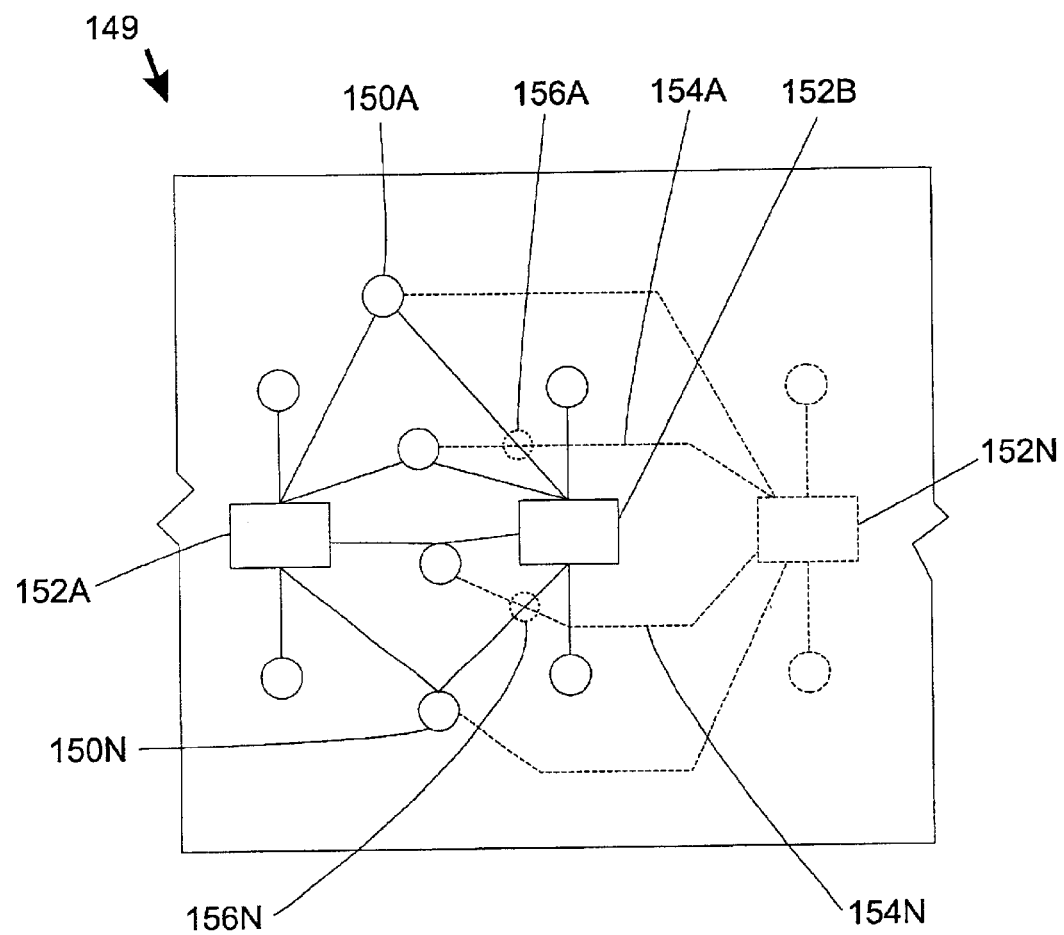
FIG._ 2C

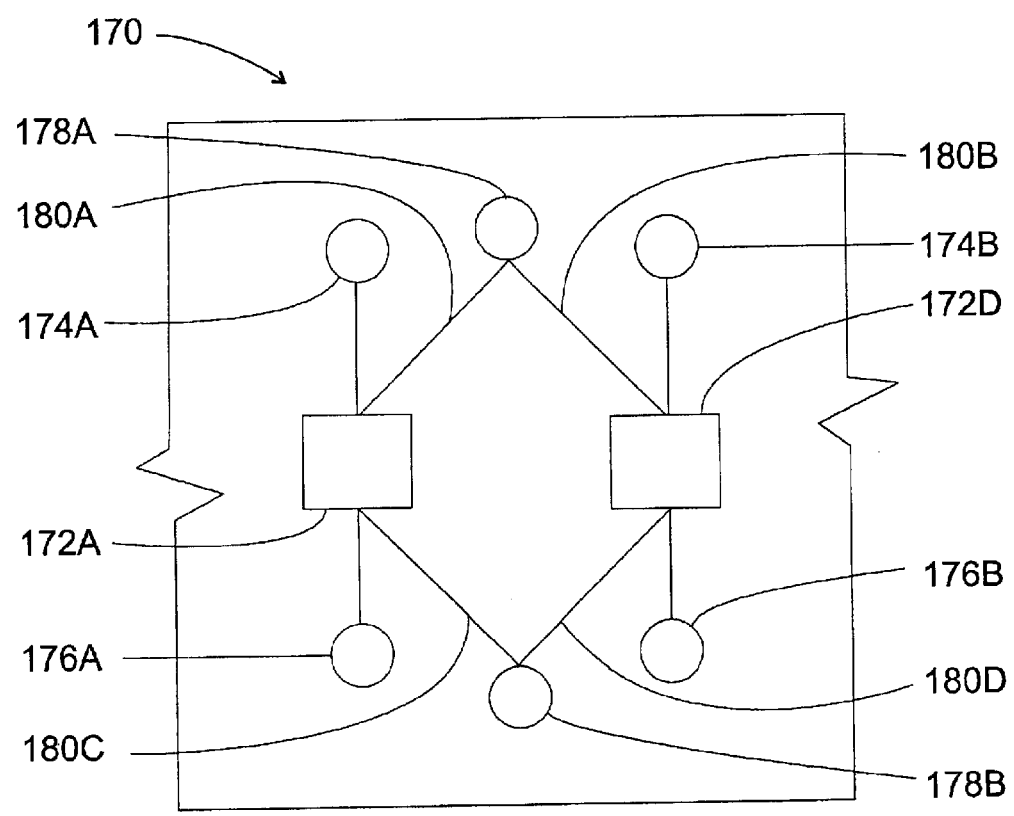
FIG._ 2D

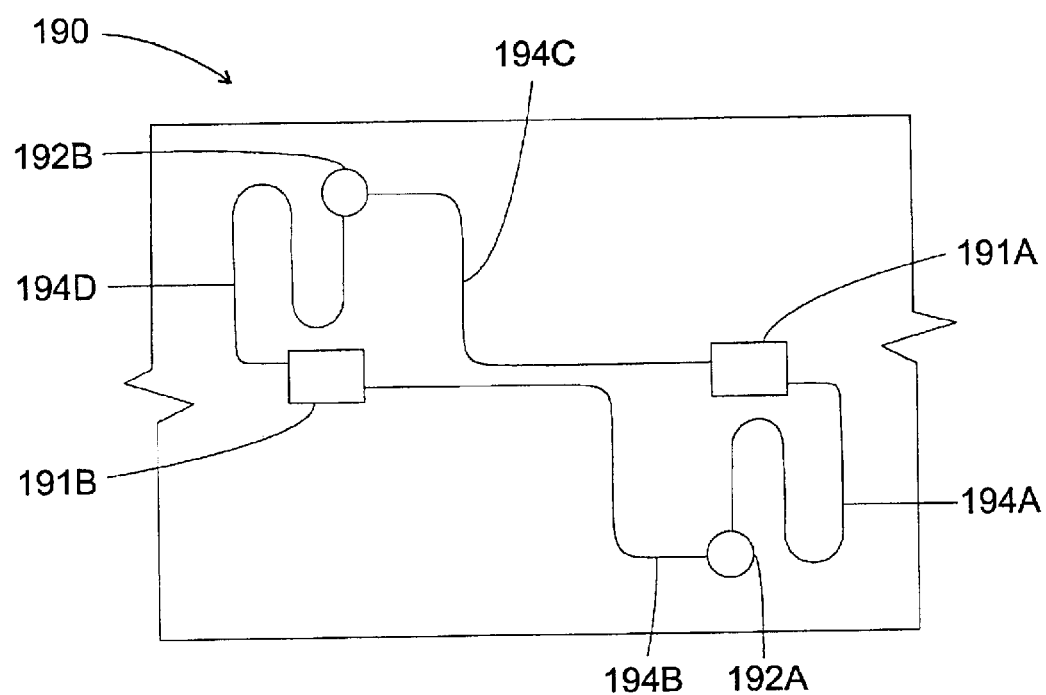
FIG._ 2E

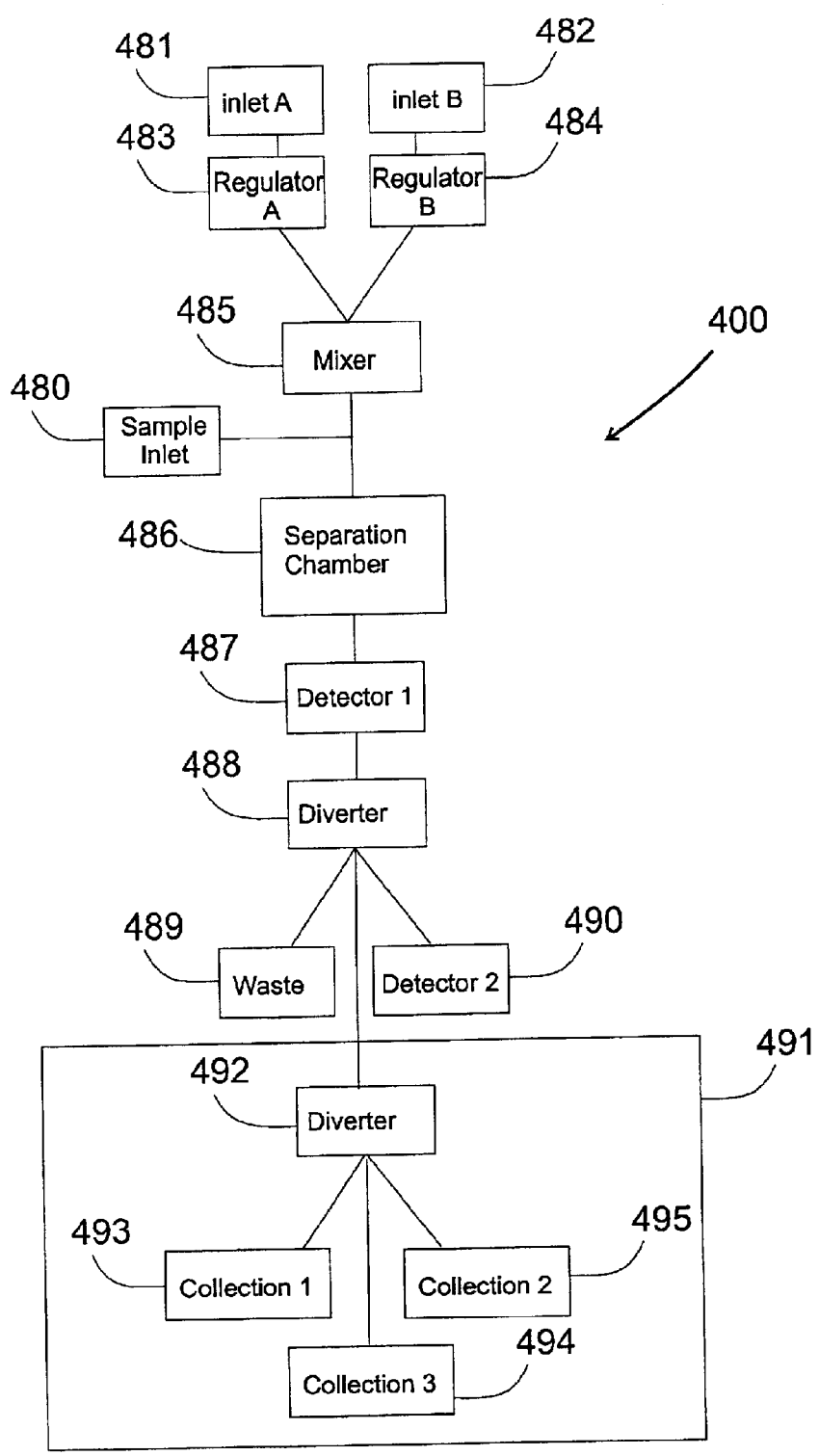
FIG._3

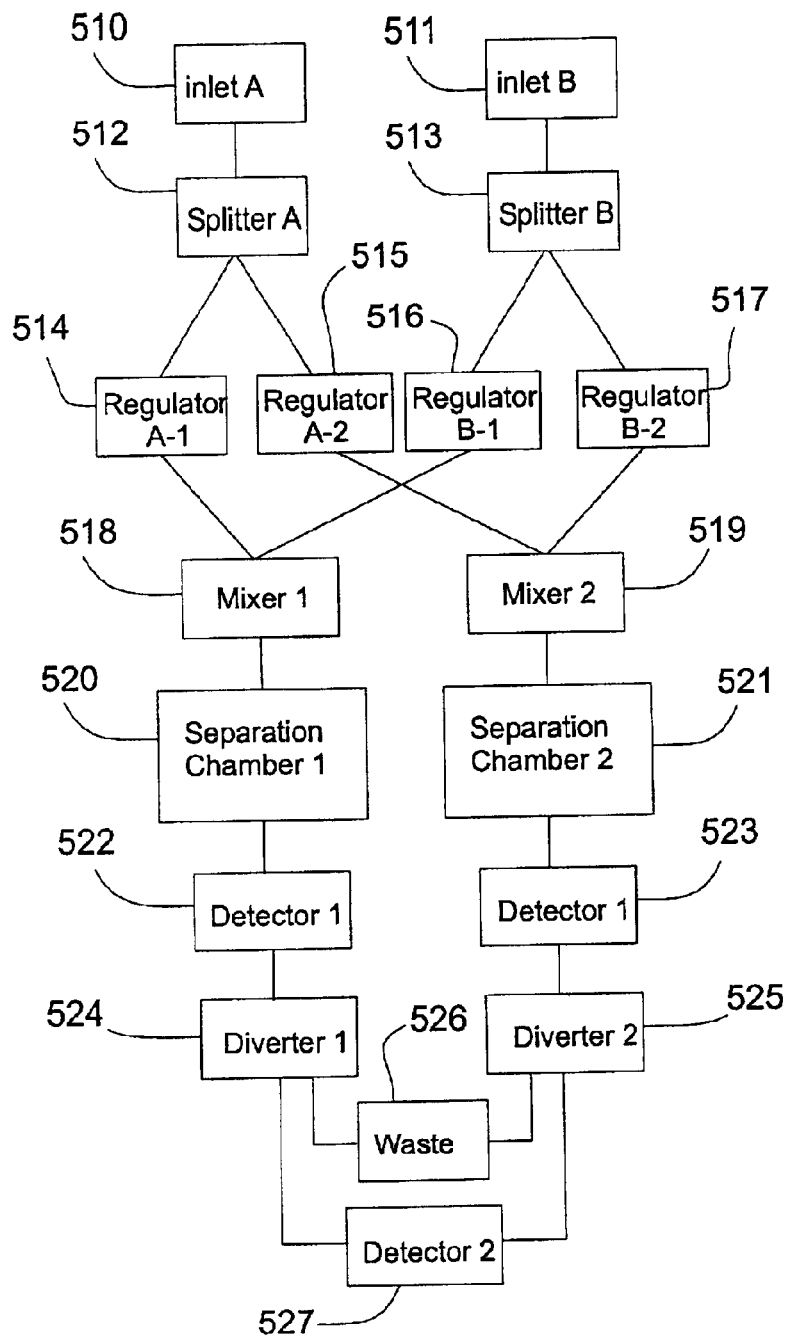
FIG._ 4

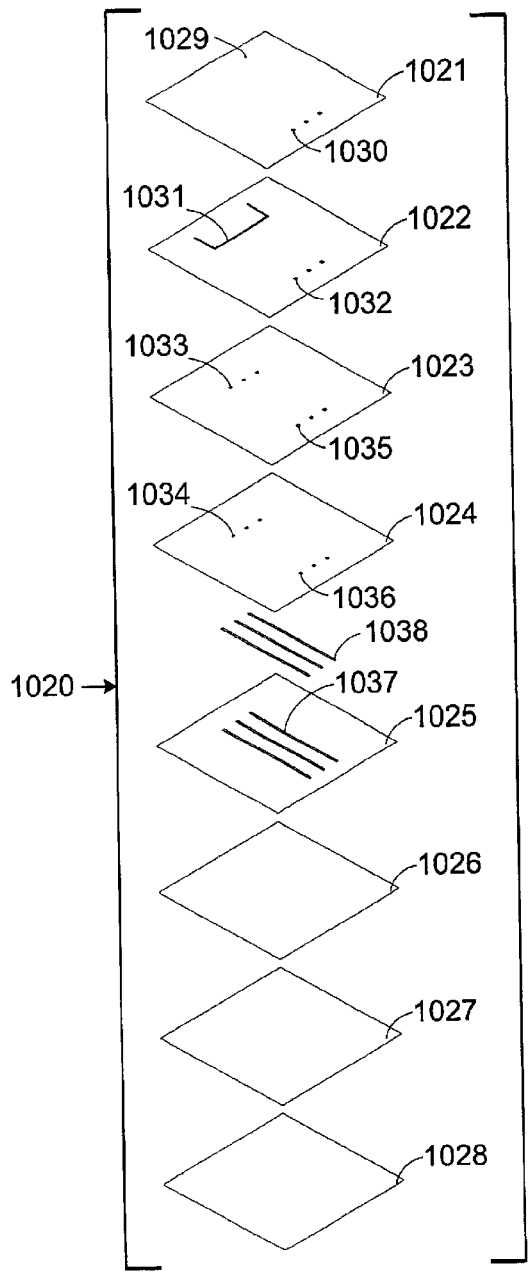
FIG._ 5A
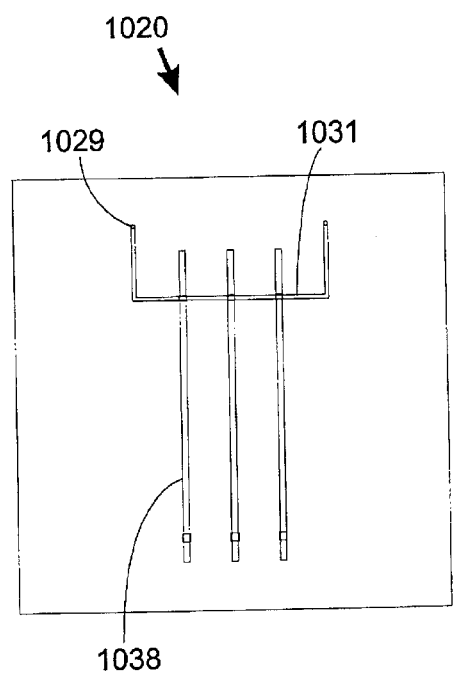
FIG._ 5B

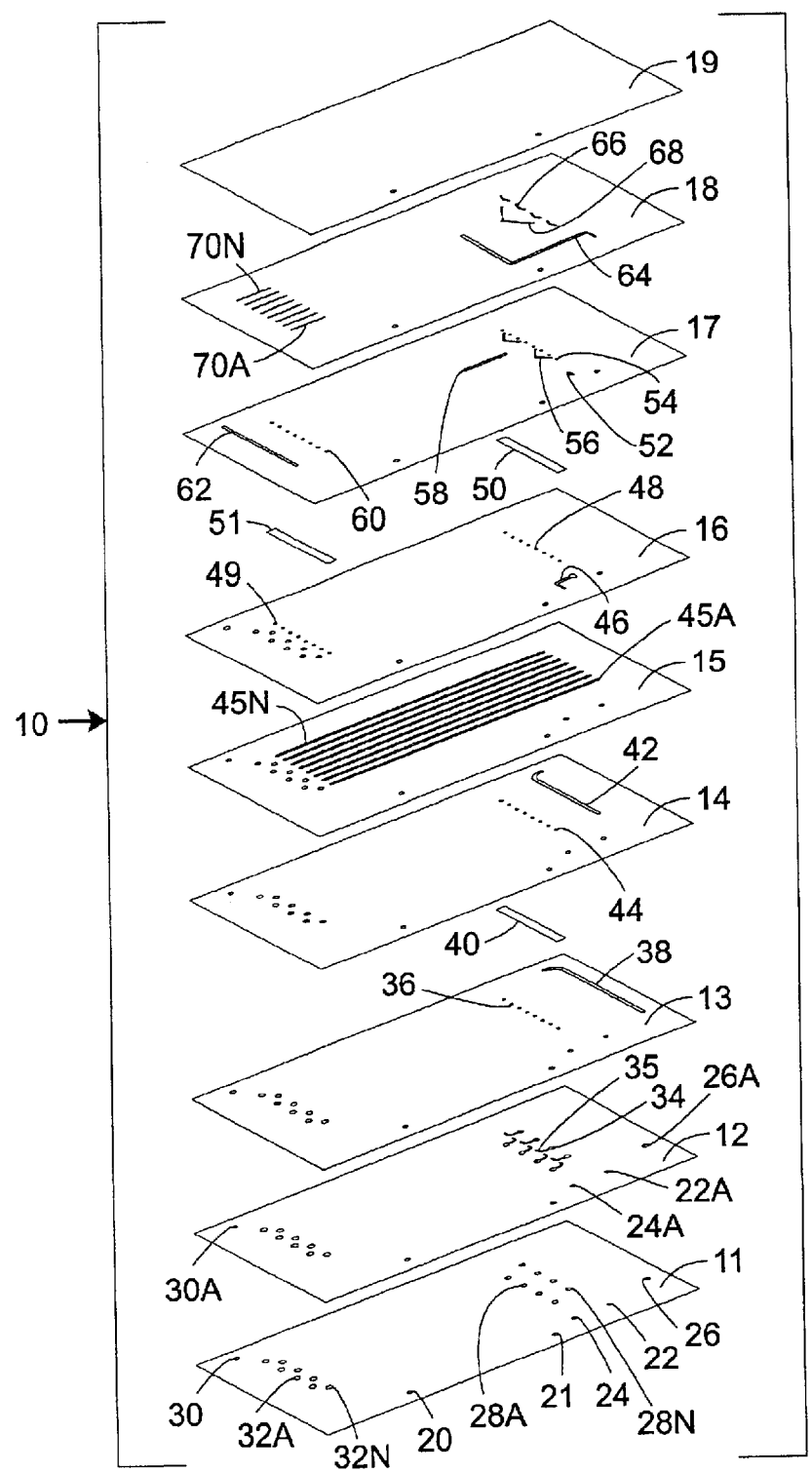
FIG._6A

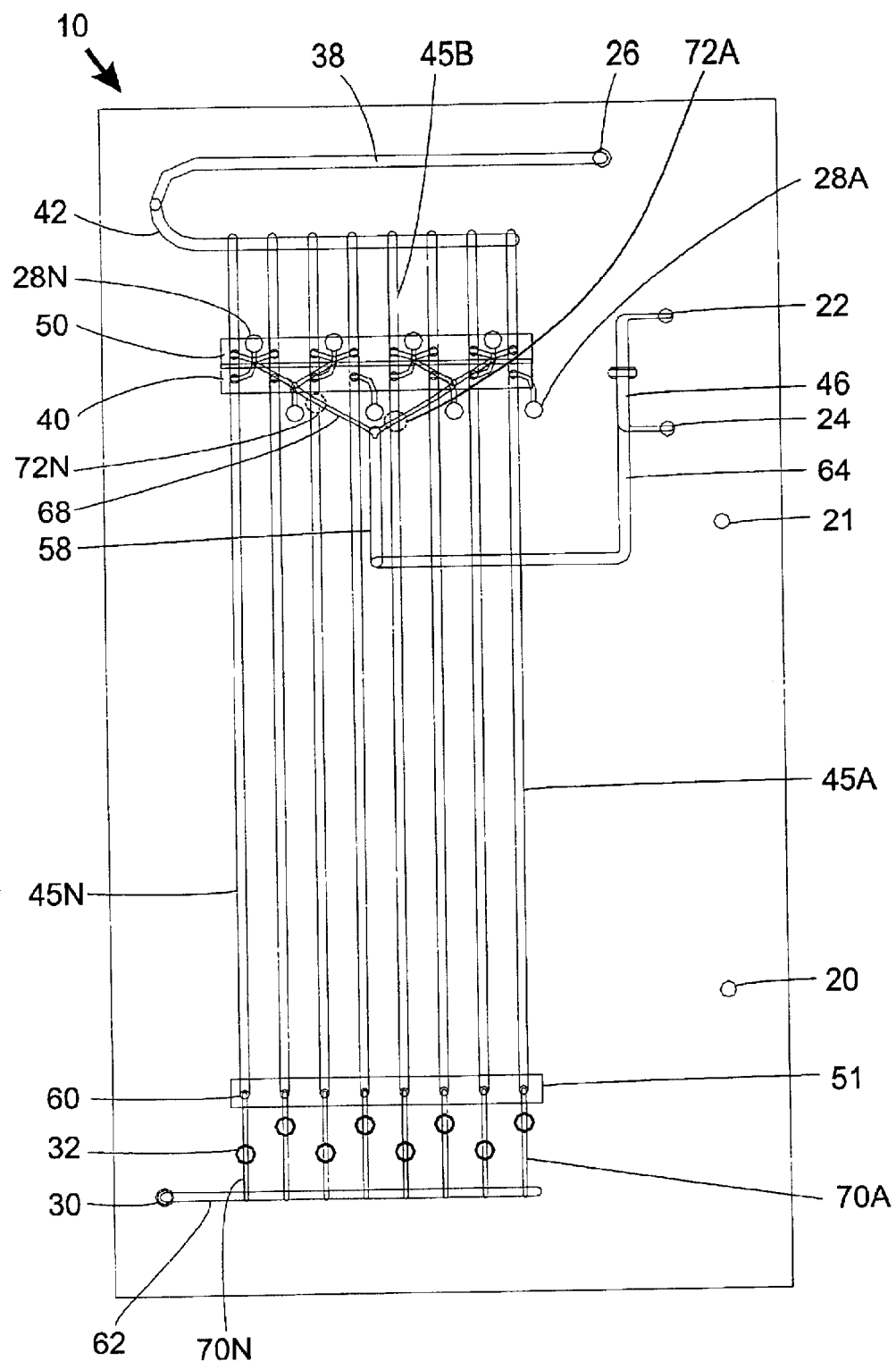
FIG._6B

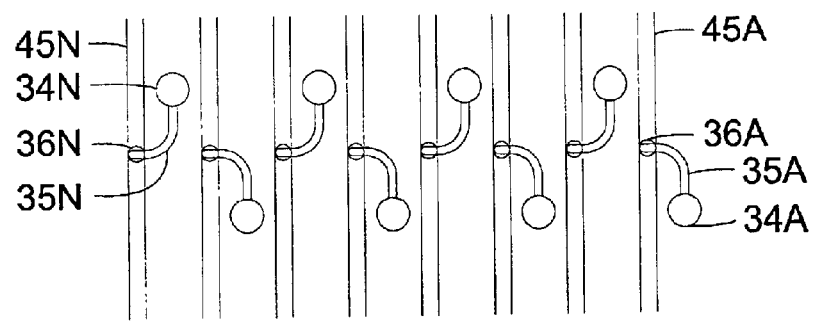
FIG._6C
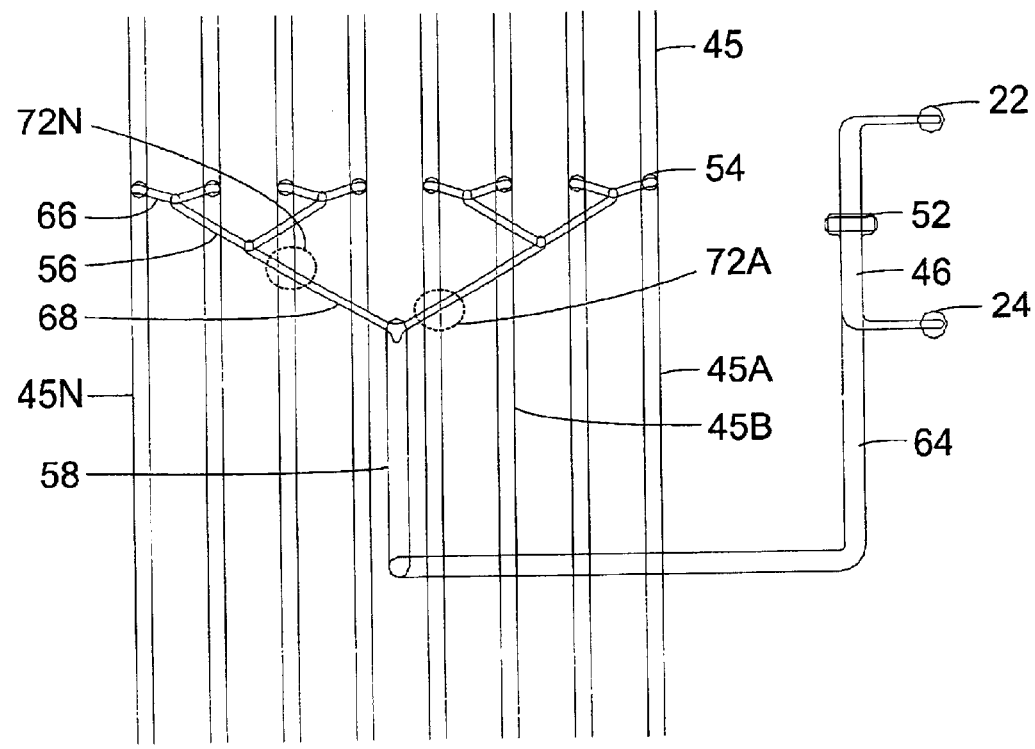
FIG._6D

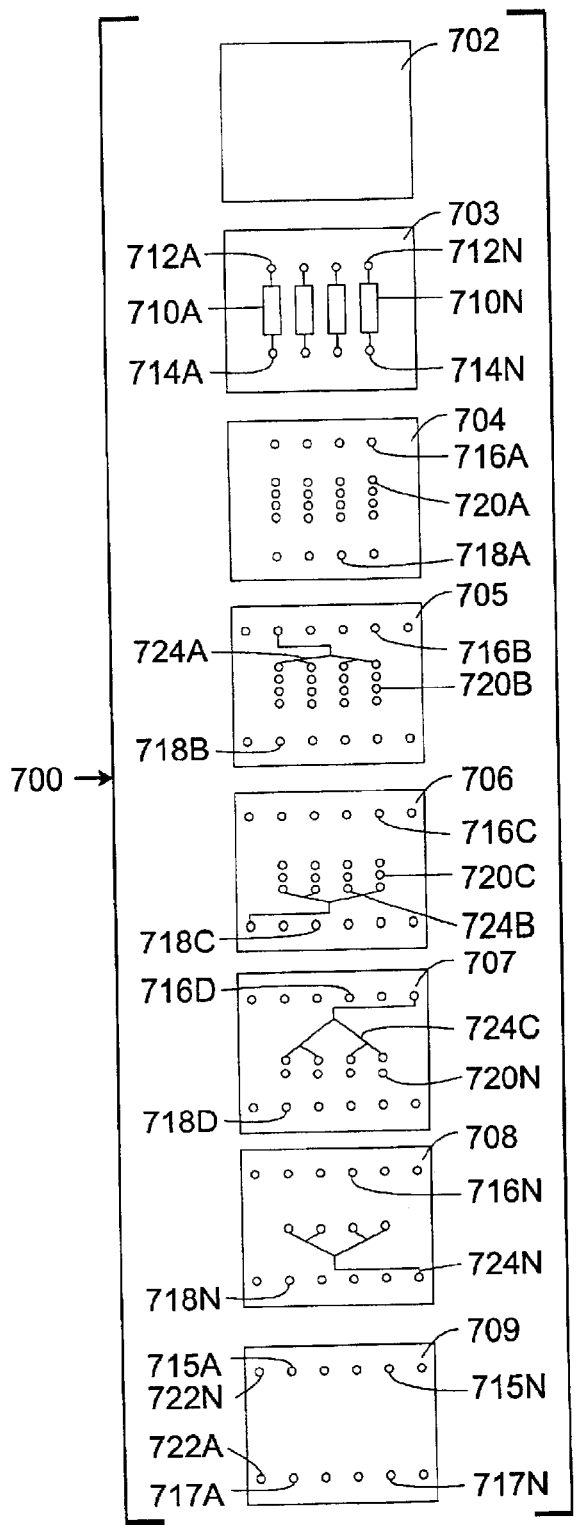
FIG._7A

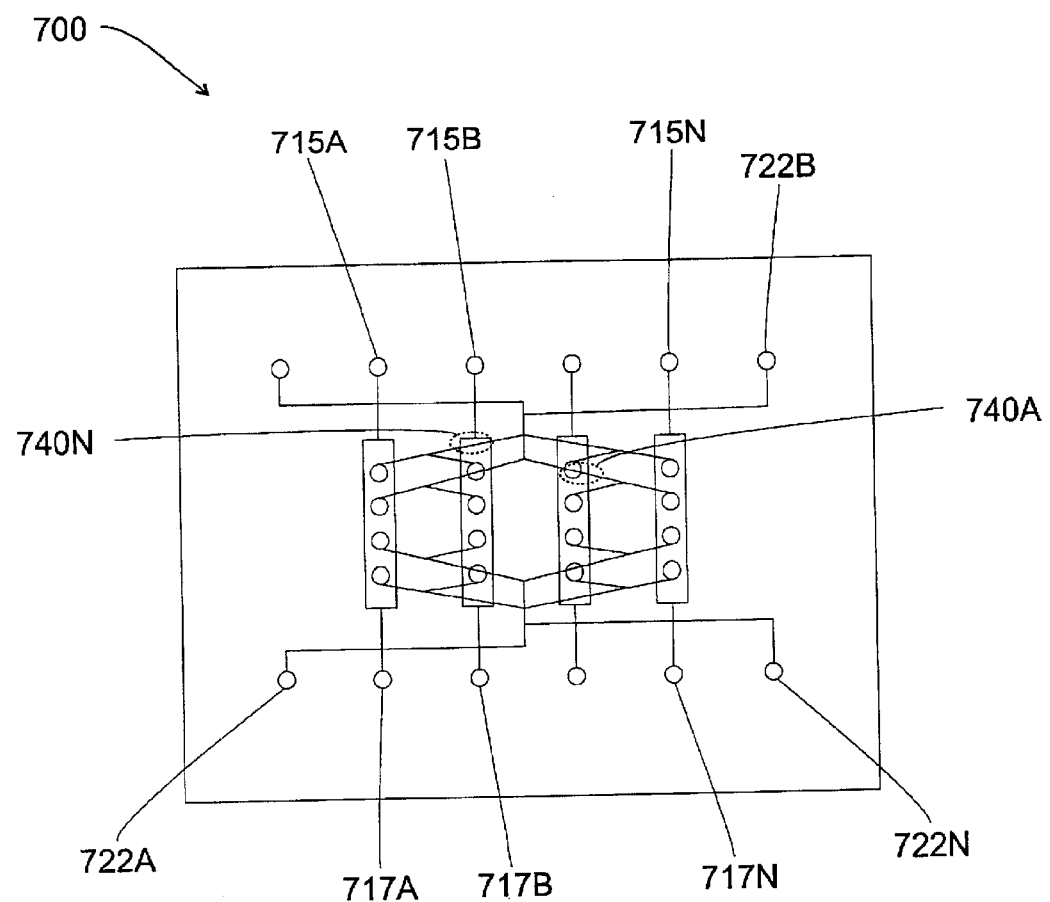
FIG._7B

MICROFLUIDIC DEVICES WITH DISTRIBUTING INPUTS

STATEMENT OF RELATED APPLICATION(S)

This application claims priority to U.S. Provisional Patent Application Ser. No. 60/296,897, filed Jun. 7, 2001 and currently pending; and U.S. Provisional Patent Application Ser. No. 60/357,683, filed Feb. 13, 2002 and currently pending.

FIELD OF THE INVENTION

The present invention relates to microfluidic devices and methods for their use and manufacture. These devices and methods are useful in performing multiple microfluidic-scale chemical and biological analyses in parallel on a single device.

BACKGROUND OF THE INVENTION

There has been a growing interest in the manufacture and use of microfluidic systems for the acquisition of chemical and biological information. In particular, when conducted in microfluidic volumes, complicated biochemical reactions may be carried out using very small volumes of liquid. Among other benefits, microfluidic systems improve the response time of reactions, minimize sample volume, and lower reagent consumption. When volatile or hazardous materials are used or generated, performing reactions in microfluidic volumes also enhances safety and reduces disposal quantities.

Traditionally, microfluidic devices have been constructed in a planar fashion using techniques that are borrowed from the silicon fabrication industry. Representative systems are described, for example, in some early work by Manz et al. (Trends in Anal. Chem. (1990) 10(5): 144–149; Advances in Chromatography (1993) 33: 1–66). In these publications, microfluidic devices are constructed by using photolithography to define channels on silicon or glass substrates and etching techniques to remove material from the substrate to form the channels. A cover plate is bonded to the top of the device to provide closure. Miniature pumps and valves can also be constructed to be integral (e.g., within) such devices. Alternatively, separate or off-line pumping mechanisms are contemplated.

More recently, a number of methods have been developed that allow microfluidic devices to be constructed from plastic, silicone or other polymeric materials. In one such method, a negative mold is first constructed, and plastic or silicone is then poured into or over the mold. The mold can be constructed using a silicon wafer (see, e.g., Duffy et al., Analytical Chemistry (1998) 70: 4974–4984; McCormick et al., Analytical Chemistry (1997) 69: 2626–2630), or by building a traditional injection molding cavity for plastic devices. Some molding facilities have developed techniques to construct extremely small molds. Components constructed using a LIGA technique have been developed at the Karolsruhe Nuclear Research center in Germany (see, e.g., Schomburg et al., Journal of Micromechanical Microengineering (1994) 4: 186–191), and commercialized by Micro-Parts (Dortmund, Germany). Jenoptik (Jena, Germany) also uses LIGA and a hot-embossing technique. Imprinting methods in PMMA have also been demonstrated (see, Martynova et al, Analytical Chemistry (1997) 69: 4783–4789) However, these techniques do not lend themselves to rapid prototyping and manufacturing flexibility. Additionally, the foregoing references teach only the preparation of planar microfluidic structures. Moreover, the tool-up costs for both of these techniques are quite high and can be cost-prohibitive.

Various conventional tools and combinations of tools are used for separations and detections when performing analyses in conventional macroscopic volumes. Such tools include, for example: filters, metering devices, columns, valves, sample injectors, heaters, coolers, mixers, splitters, diverters, and electrodes (such as are used to induce electrokinetic flow and to perform electrophoretic separations). Attempts to conduct separations or detections in microfluidic volumes have been stifled by difficulties such as making such tools in microfluidic scale and then integrating such tools into microfluidic devices. Another difficulty is accurately measuring stoichiometric microfluidic volumes of reagents and solvents to perform analyses on a microfluidic scale. Additionally, difficulties in rapidly prototyping microfluidic devices are compounded by attempts to incorporate multiple analytical tools.

A particular challenge that has arisen in the design and fabrication of microfluidic devices is the proliferation of inputs and outputs associated with such devices. For example, PCT Patent Application WO 99/19717, entitled "Laminate Microstructure Device and Methods for Making Same," by Aclara Biosciences, Inc. (the "Aclara Application") discloses a microfluidic device, which includes multiple microfluidic structures therein. FIG. 1 illustrates a device 100 similar to that disclosed in the Aclara Application. The device 100 includes eight microfluidic structures 102A–102H. Each of the microfluidic structures 102A–102H has eleven input/output ("I/O") ports 103A–103N. Consequently, operation of the device 100 would require eighty-eight I/O connections. Furthermore, it is anticipated that microfluidic devices may include substantially more than eight microfluidic structures per device. Thus, the number of I/O connections for a more feature-dense device could be significantly higher than eighty-eight.

One benefit of microfluidic devices is the ability to perform multiple experiments in a small area. The large number of I/O connections required by the device 100 would have a tendency to either expand the size of the device to accommodate the connections or complicate fabrication and operation of the device. In particular, providing a large number of I/O connections in a compact area elevates the likelihood of fabrication and/or operational errors.

The microfluidic devices described herein may include any number of parallel functional features and related inputs and outputs. Although the prior art and illustrative embodiments of the invention shown herein each have a particular number of such features, such features are numbered and lettered to reflect the fact that additional such features may be included. For example, in FIG. 2A, the functional features are numbered 106A–106N, where "N" represents the total number of such features included in the device 104. Whereas in the illustrated device 104 the "N" represents the third such functional feature, such a device 104 could include tens, hundreds or even more of such functional features providing the desired functionality according to the invention.

FIGS. 2A–2E use simplified block diagrams to illustrate various permutations of desirable microfluidic devices and difficulties created by the need for multiple I/O connections. FIG. 2A is a simplified representation of a device 104 similar to that shown in FIG. 1. The device 104 includes a plurality of functional features 106A–106N. A functional feature can be any structure for performing a desired fluidic operation, including, but not limited to one or more mixers, reactors, separation chambers, and any combinations thereof. Each functional feature 106A–106N has a sample input 108A–108N and an output 108A'–108N'. In addition, each functional feature 106A–106N may have a plurality of reagent inputs 110A–110N, 112A–112N, 114A–114N. For simplicity, the device 104 is shown with only one sample input, one output, and three reagent inputs for each functional feature 106A–106N; however, any number of inputs and outputs for samples and reagents may be used as necessitated by the desired fluidic function to be performed by the functional feature. Accordingly, the number of I/O connections required by such a device 104 equals the number of I/O connections per functional feature multiplied by the number of functional features.

If the functional features 106A–106N perform substantially identical operations in parallel, then it is likely that the same set of reagents will be used in each of the functional features. If the device 104 is used to perform parallel operations using the same reagents on a variety of samples, then the number of I/O connections may be reduced if inputs for reagents common to more than one functional feature are combined, as shown in FIG. 2B. A device 120 includes a plurality of functional features 122A–122N. Each functional feature 122A–122N has a sample input 124A–124N and an output 124A'–124N'. Two common reagent inputs 126, 128 provide reagents to the functional features 122A–122N. Because reagent can be provided to all functional features 122A–122N from the two inputs 126, 128, the total numbers of I/O connections for reagents can be reduced by (N−1)×Y, where "N" is the number of functional features and "Y" is the number of reagent inputs per functional feature. Thus, if the device 120 includes eight functional features with two reagent inputs for each, this approach would result in only two common reagent inputs, rather than the sixteen independent reagent inputs that would be required for a device such as that shown in FIG. 2A.

The techniques used to fabricate microfluidic devices typically rely on machining or etching the surface of a planar material to produce the desired microfluidic structure. As a result, these microfluidic structures typically are provided in a single plane. One consequence of this approach is that it becomes difficult, if not impossible, to substantially expand the functionality and complexity of the fluidic operations due to structural limitations. For example, as shown in FIG. 2B, the addition of a third common reagent input 130 (shown in ghosted lines) and channels 132, 134 to carry reagent from the input 130 to the functional features 122A–122N results in the intersection (or "channel crossing") of these channels 132, 134 with other reagent channels 136, 138 at intersection points 140, 142. Because these structures all are defined in a single plane, the channel crossings 132, 134, 136, 138 will result in unintended combining of the reagents, essentially rendering the device 120 inoperable for most scientific purposes. Likewise, as shown in FIG. 2C, a plurality of reagent inputs 150A–150N may be used to provide reagents to two functional features 152A, 152B in a device 149. If, however, further functional features 152N are added, channels 154A–154N from any reagent input 150A–150N in excess of two will result in problematic channel crossings 156A–156N.

Thus, in a two dimensional device, it is impossible to use of more than two common non-intersecting reagent inputs when more than two functional features are used. Likewise, the use of more than two functional features is impossible when more than two common non-intersecting inputs are used. Of course, it may be possible to use small hoses to allow crossing lines to "jump over" the intersection. However, such an approach would substantially increase the manufacturing complexity of such a microfluidic device as well as compound the likelihood of component failures that could render the device inoperable.

The use of common inputs, while potentially simplifying the I/O connections to a microfluidic device, also may create additional problems. As a result of the very small dimensions of microfluidic structures, fluids moving through such structures are characterized by very low Reynolds Numbers (corresponding to laminar flow) and flow dynamics that are heavily affected, if not dominated, by surface interactions. Thus, fluids in microfluidic structures often exhibit surprising and unexpected properties. For example, when fluid traveling through a microfluidic structure encounters a split or fork in a channel, the fluid may flow through only one fork or only the other—not dividing and distributing evenly between the two, as would be expected in conventional macrofluidic systems. Alternatively, the flow may split, but not evenly. As a consequence of this behavior, it may be difficult to consistently and accurately divide and distribute a reagent stream to a plurality of functional features, simply because it may be difficult to predict the particular flow paths that will be adopted by a given fluid flowing within a multi-path microfluidic structure.

It has been observed that fluid flow behavior within microfluidic structures may be influenced by the fluidic impedance encountered by the fluid. The presence and magnitude of fluidic impedance depends on a number of factors, such as interaction between the fluid and the surface of the structure ("surface interactions"); the pressure driving the fluid ("fluid pressure"); the pressure resisting fluid flow ("backpressure"); the physical arrangement of the microfluidic structure ("structural geometry"); and the characteristics of the fluid, including, but not limited to, mass, density, and viscosity ("fluid properties"). In particular, it has been noted that fluids divided and distributed from a single source or inlet (which may be a port, aperture or channel) into a plurality of branch channels tend to split evenly among the branch channels only when the impedance encountered by the fluid is substantially the same across all of the branch channels into which the fluid is being divided.

Thus, if a common input is used to divide and distribute a fluid among multiple functional features, care must be taken to match the impedance of each channel carrying reagent from the common input to each of the functional features. For example, FIG. 2D illustrates a simple microfluidic device 170 having two functional features 172A–172B. Each of the functional features 172A–172B has a sample input 174A–174B and an output 176A–176B. Two common reagent inputs 178A, 178B provide reagent to the functional features via reagent channels 180A–180D. In this simple configuration, impedance matching among channels 180A–180D is provided by positioning the reagent inputs 178A–178B equidistantly from the functional features 172A–172B, thereby matching the length of each of the channels 180A–180D to each other. So long as such a simple arrangement is possible, this approach may provide the desired results. However, as a design becomes more complex, due to, for example, increased feature density or input positions required to maintain compatibility to a particular laboratory device, such careful positioning of reagent inputs may not be possible. Thus, as shown in FIG. 2E, in a device 190, having two functional features 191A–191B and common reagent inputs 192A–192B, it may be necessary to provide convoluted reagent channels 194A–194D. The convolutions of the reagent channels 194A–194D allow the channels 194A–194D to be the same length (therefore having substantially the same impedance, assuming that the other channel characteristics are constant) even though the reagent inputs 192A–192B are not equidistant from each of the functional features 191A–191B.

If the feature density increases substantially, however, the convolutions required to provide the desired impedance matching may become very complex, thereby complicating the design, fabrication, operation and validation of the device. Furthermore, any such device remains constrained by the channel intersection problem described above.

In addition, the vast array of microfluidic tools and designs available today and anticipated in the future can present an infinite number of I/O interface configurations. For example, in each of the examples described above it can be seen that the pattern of inputs and outputs for samples and reagents differs substantially from device to device. Moreover, in order to maintain impedance matching among common inputs and/or to avoid undesirable channel intersections, the actual positioning of these inputs and outputs may be driven by the function of the device rather than the interface of existing laboratory tools. Thus, connection of highly parallel microfluidic devices to existing tools may require customized interfaces and/or complexes of flexible tubing to allow connection to other devices and/or laboratory tools and instruments. Such interface requirements tend to enlarge the footprint of the device, complicate operation, complicate manufacture of the device and/or increase the complexity of other devices used in conjunction with the device.

Thus, it would be desirable to provide microfluidic devices with minimal numbers of I/O connections. It also would be desirable to provide microfluidic devices that accurately and reliably divide and distribute fluidic inputs to the various structures within the device. It also would be desirable to provide microfluidic devices that readily interface with existing laboratory tools.

SUMMARY OF THE INVENTION

In a first separate aspect of the present invention, a multi-layer microfluidic device includes: a plurality of device layers defining at least three functional features; a first, a second, and a third distributing input, each associated with each of the at least three functional features; and a channel crossover region. The channel crossover region includes: a first distribution channel (the first distribution channel defined in a first device layer); a second distribution channel (the second distribution channel defined in a second device layer); and a third device layer disposed between the first device layer and the second device layer. The third device layer prevents fluid communication between the first channel and the second channel at the channel crossover region.

In another separate aspect of the invention, a multi-layer microfluidic device includes at least three functional features, at least three distributing inputs each having a plurality of channels, a plurality of channel crossings, and an intervening device layer. Each distributing input is in fluid communication with the functional features. The intervening device layer preventing fluid communication between any of the distributing inputs at any channel crossing.

In another separate aspect of the invention, a multi-layer microfluidic device includes a functional device layer defining at least three functional features. A first device layer has a first set of distribution channels in fluid communication with the functional features. A second device layer has a second set of distribution channels in fluid communication with the functional features. A third device layer has a third set of distribution channels in fluid communication with the at least three functional features. The second device layer is disposed between the first device layer and the third device layer.

In another separate aspect of the invention, a multi-layer microfluidic device comprises a first device layer defining at least three functional features and a first distributing input in fluid communication with each of the at least three functional features. A second device layer defines a second distributing input in fluid communication with each of the at least three functional features. A third distributing input, defined one of the first device layer or the second device layer, is in fluid communication with each of the at least three functional features. A third device layer is disposed between the first device layer and the second device layer.

In another separate aspect of the invention, any of the foregoing separate aspects may be combined for additional advantage. These and other aspects and advantages of the invention will be apparent to the skilled artisan upon review of the following description, drawings and claims.

BRIEF DESCRIPTION OF THE DRAWINGS

FIG. 2A is a block diagram illustrating a planar, two-dimensional microfluidic device having multiple independent inputs and multiple functional features. FIG. 2B is a block diagram illustrating a planar, two-dimensional microfluidic device having multiple independent inputs, two common inputs, and multiple functional features. FIG. 2C is a block diagram illustrating a planar, two-dimensional microfluidic device having independent inputs, multiple common inputs, and two functional features. FIG. 2D is a block diagram illustrating a planar, two-dimensional microfluidic device having independent inputs, two impedance-matched common inputs, and two functional features. FIG. 2E is a block diagram illustrating a planar, two-dimensional microfluidic device having independent inputs, two impedance-matched common inputs, and two functional features.

FIG. 3 is a block diagram illustrating the operation of a multi-layer, three-dimensional microfluidic device according to one embodiment of the present invention.

FIG. 4 is a block diagram illustrating the operation of a multi-layer, three-dimensional microfluidic device according to another embodiment of the present invention.

FIG. 5A is an exploded perspective view of a multi-layer, three-dimensional microfluidic device according to another embodiment of the present invention. FIG. 5B is a top view of the assembled device of FIG. 5A.

FIG. 6A is an exploded perspective view of a multi-layer, three-dimensional microfluidic device according to another embodiment of the present invention. FIG. 6B is a top view of the assembled device of FIG. 6A. FIG. 6C is an enlarged top view of a first portion of the device of FIGS. 6A–6B. FIG. 6D is an enlarged top view of a second portion of the separation device of FIGS. 6A–6B.

FIG. 7A is an exploded perspective view of a multi-layer, three-dimensional microfluidic device according to another embodiment of the present invention. FIG. 7B is a top view of the assembled device of FIG. 7A.

DETAILED DESCRIPTION OF PREFERRED EMBODIMENTS

Definitions

Figure 1:
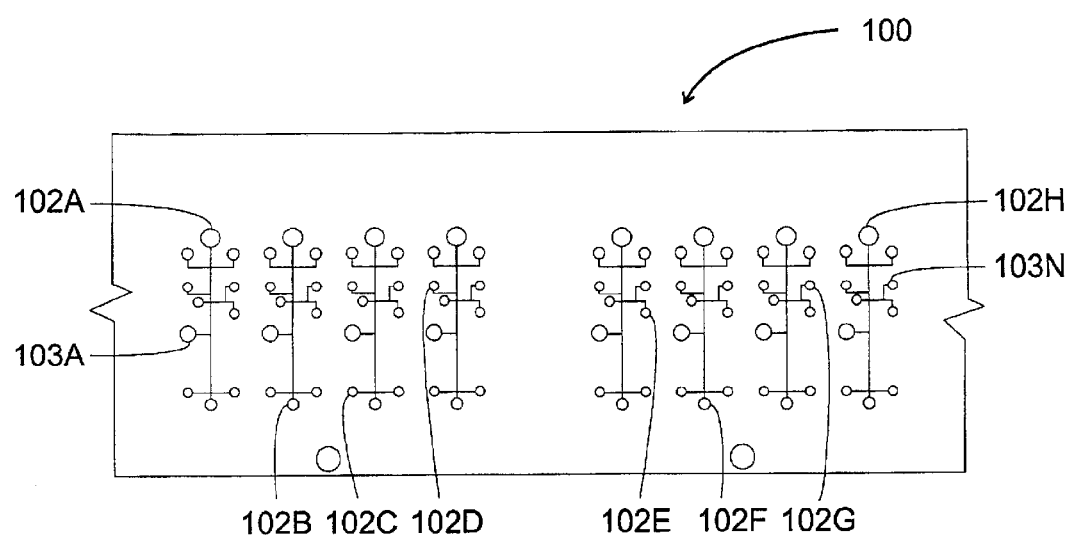
FIG. 1 is a top view of a microfluidic device of the prior art.

The term "channel" or "chamber" as used herein is to be interpreted in a broad sense. Thus, it is not intended to be restricted to elongated configurations where the transverse or longitudinal dimension greatly exceeds the diameter or cross-sectional dimension. Rather, such terms are meant to comprise cavities or tunnels of any desired shape or configuration through which liquids may be directed. Such a fluid cavity may, for example, comprise a flow-through cell where fluid is to be continually passed or, alternatively, a chamber for holding a specified, discrete ratio of fluid for a specified ratio of time. "Channels" and "chambers" may be filled or may contain internal structures comprising, for example, valves, filters, and similar or equivalent components and materials.

The term "distributing input" as used herein refers to a fluidic inlet that divides and distributes a fluid among multiple functional features. A distributing input typically includes a common fluidic region (e.g., a port, an aperture, or equivalent structure) and multiple distribution channels that branch outward from the common fluidic region.

The term "functional feature" as used herein refers to any microfluidic structure within a microfluidic device that performs an operation on, or permits interaction with, fluids introduced into the device. For example, functional features may include, but are not limited to, mixers, separation channels, reaction chambers, analysis windows, and other useful structures known in the art.

The term "microfluidic" as used herein is to be understood, without any restriction thereto, to refer to structures or devices through which fluid(s) are capable of being passed or directed, wherein one or more of the dimensions is less than 500 microns.

The terms "stencil" or "stencil layer" as used herein refers to a material layer or sheet that is preferably substantially planar, through which one or more variously shaped and oriented channels have been cut or otherwise removed through the entire thickness of the layer, thus permitting substantial fluid movement within the layer (as opposed to simple through-holes for transmitting fluid through one layer to another layer). The outlines of the cut or otherwise removed portions form the lateral boundaries of microstructures that are completed when a stencil is sandwiched between other layers, such as substrates and/or other stencils. Stencil layers can be either substantially rigid or flexible (thus permitting one or more layers to be manipulated so as not to lie in a plane).

Microfluidic Devices Generally

In an especially preferred embodiment, microfluidic devices according to the present invention are constructed using stencil layers or sheets to define channels and/or chambers. As noted previously, a stencil layer is preferably substantially planar and has a channel or chamber cut through the entire thickness of the layer to permit substantial fluid movement within that layer. Various means may be used to define such channels or chambers in stencil layers. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut portions through a material layer. While laser cutting may be used to yield precisely dimensioned microstructures, the use of a laser to cut a stencil layer inherently involves the removal of some material. Further examples of methods that may be employed to form stencil layers include conventional stamping or die-cutting technologies, including rotary cutters and other high throughput auto-aligning equipment (sometimes referred to as converters). The above-mentioned methods for cutting through a stencil layer or sheet permits robust devices to be fabricated quickly and inexpensively compared to conventional surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers are intended to mate with one or more adjacent layers (such as stencil layers or substrate layers) to form a substantially enclosed device, typically having at least one inlet port and at least one outlet port.

A wide variety of materials may be used to fabricate microfluidic devices having sandwiched stencil layers, including polymeric, metallic, and/or composite materials, to name a few. Various preferred embodiments utilize porous materials including filter materials. Substrates and stencils may be substantially rigid or flexible. Selection of particular materials for a desired application depends on numerous factors including: the types, concentrations, and residence times of substances (e.g., solvents, reactants, and products) present in regions of a device; temperature; pressure; pH; presence or absence of gases; and optical properties.

Various means may be used to seal or bond layers of a device together. For example, adhesives may be used. In one embodiment, one or more layers of a device may be fabricated from single- or double-sided adhesive tape, although other methods of adhering stencil layers may be used. Portions of the tape (of the desired shape and dimensions) can be cut and removed to form channels, chambers, and/or apertures. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thickness of these carrier materials and adhesives may be varied.

In another embodiment, device layers may be directly bonded without using adhesives to provide high bond strength (which is especially desirable for high-pressure applications) and eliminate potential compatibility problems between such adhesives and solvents and/or samples. Specific examples of methods for directly bonding layers of non-biaxially-oriented polypropylene to form stencil-based microfluidic structures are disclosed in co-pending U.S.

Provisional Patent Application Ser. No. 60/338,286 (filed Dec. 6, 2001), which is owned by assignee of the present application and incorporated by reference as if fully set forth herein. In one embodiment, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately 5 hours at a temperature of 154° C. to yield a permanently bonded microstructure well-suited for use with high-pressure column packing methods.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

Further embodiments may be fabricated from various materials using well-known techniques such as embossing, stamping, molding, and soft lithography.

In addition to the use of adhesives and the adhesiveless bonding method discussed above, other techniques may be used to attach one or more of the various layers of microfluidic devices useful with the present invention, as would be recognized by one of ordinary skill in attaching materials. For example, attachment techniques including thermal, chemical, or light-activated bonding steps; mechanical attachment (such as using clamps or screws to apply pressure to the layers); and/or other equivalent coupling methods may be used.

Preferred Embodiments

Microfluidic devices according to the invention may be provided to perform any desirable fluidic operation, including, without limitation, synthesis and analysis of chemical or biological species. These microfluidic devices are characterized by a plurality of functional features for performing one or more fluidic operations. Each functional feature may have independent inputs for introduction of samples, reagents or other useful fluids required to perform the operative function(s) of the functional feature. Independent outputs allow products of the operation(s) to be analyzed, collected, disposed of, or transferred to other functional features, laboratory instruments, or other desirable locations. If the product is to be discarded, then the outputs may be merged into a common waste channel.

Reagents, samples, or other fluids common to multiple functional features ("common fluids") may be input into a microfluidic device or system through one or more distributing inputs that divide and distribute the common fluids as desired. The use of a multi-layer fabrication technique allows multiple such distributing inputs to distribute to multiple functional features in a device without undesirable intersection of fluid channels. This capability arises as a consequence of the three-dimensional character of multilayer devices, which allows two or more channels to cross each other with a device layer disposed and preventing fluid communication therebetween.

According to one embodiment of the invention, a microfluidic analytical device provides both separation and detection capabilities. A schematic diagram of one embodiment of the present invention is shown in FIG. 3. This schematic diagram describes a general analytical technique for the current invention. As would be appreciated by one skilled in the art, variations on this theme are possible as certain individual steps may be rearranged or omitted for particular applications. Referring to FIG. 3, a device 400 includes two inlet ports 481, 482 provide solvent to two regulators 483, 484 that feed a mixer 485. Downstream of the mixer 485 is a separation chamber 486. A sample inlet port 480 delivers sample to the device 400 between the mixer 485 and the separation chamber 486. Alternatively, the sample may be injected within the separation chamber 486. In a further alternative embodiment, sample may be injected using one of the solvent inlets 481, 482. In another embodiment, the solvent may be mixed "off-board," necessitating only one solvent inlet. More solvent inlets can be added to increase the complexity of the solvent mixture. Moreover, multiple devices 400 may be combined on a single microfluidic platform so that multiple operations may be performed in parallel. When it is desirable to perform the functions provided by the device 400 in parallel in a single microfluidic device or system, distributing inputs may be incorporated so that solvents and other fluids common to two or more of the parallel operations may be introduced into the platform at a single point and distributed to each device as desired.

The mixing region 485 effectively mixes the solvent before it reaches the separation chamber 486. The separation chamber 485 can be configured in a variety of ways, as would be recognized by one skilled in the art, to perform techniques such as ion exchange, gel filtration or size exclusion, adsorption, partition, chromatofocusing, and affinity chromatographies. In one embodiment, the separation chamber 486 is a straight channel filled with stationary phase material. The length of the channel may be varied as needed to perform the desired separation.

The exit of the separation chamber 486 leads to the initial flow-through detector 487. Preferably, the detector 487 is external to the device 400. Alternatively, on-board detection may be provided. The flow-through detection scheme will typically be set up so that molecules or atoms of interest can be detected while the fluid is still flowing in the device 400. Examples of the flow-through detectors 487 include but are not limited to UV-visible spectroscopy, Raman spectroscopy, fluorescence detection, chemiluminescence, electrochemical detection, and other electronic detections such as capacitive and conductivity measurement.

The flow-through detector 487 may be used to pre-screen the fluid as it comes off the separation chamber 486 to determine if the given fluid has molecules of interest for further analysis or storage. In FIG. 3, a flow-through detector 487 leads to a diverter module 488 which can direct the fluid to a waste chamber 489, a secondary detector module 490, or a fraction collector 491. The fraction collector 491 contains an additional diverter 492 and a number of collection chambers 493–495. A larger or smaller number of collection chambers may be used.

The secondary detector 490 may utilize a destructive detection technology such as mass spectrometry, nuclear magnetic resonance, evaporative light scattering, ion mobility spectrometry, or immobilization on material such as glycerol or porous silicon for matrix assisted laser desorption ionization ("MALDI"). It may be necessary for the detector 490 to have an off-board collection mechanism, such as collection into a vial, capillary tube, hose, etc. that leads to the detector 490. Alternatively, a sampling mechanism can be built into the microfluidic device so that the sample is directly injected into an off-board detection system. For example, the outlet of the diverter 488 can lead to an open port to be used for electrospray.

In a preferred embodiment of the present invention, a parallel processing microfluidic analytical device is constructed. The term "parallel processing" as used herein refers to multiple microfluidic systems on a given contiguous device wherein some or all of the systems are in fluid communication with one another. In a preferred embodiment, multiple fluidic inlets are provided to a parallel processing microfluidic device. In another embodiment, multiple outlets, distributing inlets, and/or detectors are in communication with more than one microfluidic systems on a given device. In these embodiments, a variety of simultaneous analytical processes may be accomplished using a small number of control inputs or outputs.

In another embodiment, a plurality of analytical separation chambers or channels reside on a single microfluidic device. This plurality of separation chambers are connected to microfluidic inlet ports that are used to insert samples for separation. The inlet ports for sample injection and solvent injection can be the same ports or different ports. In a preferred embodiment of the invention, the plurality of separation chambers are connected in such a way that a single sample injection port may deliver fluid to a plurality of separation chambers. In this manner, sample can be injected at a single macroscopic connection but be loaded onto a multitude of chambers.

In another embodiment, a multitude of separation chambers can be connected to a small number of solvent inlets that simultaneously or serially apply solvent in known mixtures to said separation chambers. In this manner, a small number of "off-board" pumps can be used to control a multitude of separation chambers.

Referring to FIG. 4, a schematic illustrating a parallel processing microfluidic analysis system according to one embodiment is shown. The system has distributing inputs 510, 511 that are connected to splitters 512, 513. Each splitter is connected to two regulators 514–517 for individually regulating the pressure and/or flow of solvent to each of the mixers 518, 519. In a preferred embodiment, the regulators 514–517 are externally controlled so that the user can specify the mixing ratios of fluids A and B when they reach the mixers 518, 519. In another preferred embodiment, the regulators 514–517 are fixed so that a known constant mixing ratio will be achieved at the outlet of each mixer module. In FIG. 4, a sample inlet is not illustrated, but one or more inlets can be provided in various locations. In one embodiment, a sample is injected to both separation chambers 520, 521. In another embodiment, multiple samples are injected. The mixers 518, 519 lead to two separation chambers 520, 521. The separation media can be composed of a variety of components or single components. Each separation chamber has an individual flow-through detector 522, 523. The flow-through detectors may be of various types. In one embodiment, off-board detectors that scan from one channel to the other are used. Very fast scanning can be accomplished with appropriate optics, as will be recognized by one skilled in the art.

Alternatively, both channels 522, 523 can be probed simultaneously. This probing can be accomplished by various methods such as scanning or splitting a single light source, or by providing multiple light sources or other detectors. In a preferred embodiment, a non-invasive detection technology (such as UV-visible absorption) using off-board components is used to probe the fluid immediately past the separation chambers 520, 521. Then, if a molecule of interest is detected using the off-board detector, the diverters 524, 525 may send the fluid to a secondary detector 527 (possibly using destructive methods). Alternatively, if no signal of interest is detected, then the sample may be diverted to a waste chamber 526. Other components such as a fraction collector could be added.

The embodiment shown in FIG. 4 would allow two pumps to control the solvents for two parallel fluid circuits. To accomplish the same result in a non-parallel manner, four pumps would be required. While it is possible to provide and operate multiple parallel fluid circuits on a single microfluidic device, as the number of fluid circuits increases, it becomes problematic to increase the number of inlet ports, pumps, and detectors at the same rate. In many applications, these off-board systems are expensive and large. Thus, if it is desired to simultaneously perform 100 separations, a parallel device would require 200 inlet ports, 200 pumping systems, 100 waste chambers and 100 detectors. It is therefore illustrated that the use of distributing inputs enables simplified implementation of multiple analyses on a single microfluidic device.

In embodiments described above, a multitude of separation chambers can be added by simply increasing the number of on-board regulators, splitters, mixers, and diverters. These on-board components can be built into the chip and be microfluidic in nature, if desirable in a particular application. In this manner, the number of inlet ports and off-board pumps and detectors remains constant.

While microfluidic tools and devices provided herein have been applied to perform analyses, they may also be combined and/or integrated with further tools to perform syntheses. Modular or integrated microfluidic devices having regions for performing syntheses and analyses are contemplated.

Referring to FIGS. 5A–5B, a multi-column microfluidic liquid chromatography (LC) device 1020 was fabricated in eight device layers 1021–1028 using a sandwiched stencil construction method. A laser cutter was used to cut and define various holes and channels in the layers of the device 1020. The first device layer 1021, made of 10-mil (250 micron) thickness polyester film, included injection ports 1029 and column outlet ports 1030. The second device layer 1022 was a 5.8-mil (147 micron) double-sided tape with a polyester carrier and rubber adhesive to adhere to the first and third device layers 1021, 1023. The second device layer 1022 included an injection channel 1031 having a segment perpendicular to the columns 1038 (placed into the fifth device layer 1025), and vias 1032 connecting to the column outlet ports 1032. Both the third and fourth device layers 1023, 1024 included injection vias 1033, 1034 and outlet vias 1035, 1036 in the same configuration. The second device layer 1022 was a 0.8-mil (20 micron) polyester film, and the third, fourth, sixth, and seventh device layers 1023, 1024, 1026, 1027 were made from 4-mil (100 micron) modified polyolefin thermoplastic adhesive. Alternatively, a thicker thermoplastic adhesive device layer, if available, could be substituted for the third and fourth device layers 1023, 1024 (and likewise for the sixth and device seventh layers 1026, 1027) to provide enough thermoplastic material to seal any gaps around the columns 1038. The fifth device layer 1025 was made of a 10-mil (250 micron) polyester film from which several separation channels 1037, each 40-mils wide, were defined. 40-mil (1 mm) width strips 1038 of polyester coated with silica gel, approximately 17 mils (430 microns) thick including a 250 $\mu$m coating thickness (Whatman Inc., Clifton, N.J., Cat. No. 4410 221) were placed into the respective channels 1037 to serve as liquid chromatography stationary phase material. The eighth device layer 1028 was a rigid substrate. Gaps around the LC columns 1038 were sealed to prevent leakage by laminating the thermoplastic layers (the fourth, sixth, and seventh device layers 1023, 1024, 1026, 1027) around the fifth device layer 1025 using a conventional pouch-laminating machine.

Following assembly of all device layers, the device 1020 was re-laminated to ensure that any spaces around the columns 1038 were filled. Notably, while only three separation channels 1037 having stationary phase material 1038 (collectively, "columns") are illustrated in the device 1020, other embodiments according to similar designs may be easily constructed with a multitude of columns, without any loss of performance.

It should be noted, however, that the device 1020, while taking advantage of the multi-layer construction to position fluid channels as desired, does not provide impedance-matched input channels to each of the separation columns. In another embodiment of the present invention, a preferred means of providing substantially the same impedance among multiple branch channels is to present to the fluid substantially identical structural geometries at any point at which an inlet channel encounters one or more branch channels ("branching junction"). Thus, a fluid encountering a branching junction will be directed into a plurality of branch channels, each presenting a substantially identical geometric interface to the inlet channel. The structural geometry includes such factors as the length of the branch channel, diameter of the interface, changes in direction and angle of the fluid flow, etc. In a preferred embodiment, such substantial identity of structural geometry may be provided by means of a topologically symmetrical structure.

FIGS. 6A–6B illustrate a microfluidic separation device 10 constructed with nine layers 11–19, including multiple stencil layers 12–18. Each of the nine layers 11–19 defines two alignment holes 20, 21, which are used in conjunction with external pins (not shown) to aid in aligning the layers during construction or in aligning the device 10 with an external interface during a packing process. The first layer 11 defines several fluidic ports: two inlet ports 22, 24 are used to admit mobile phase solvent to the device 10; eight sample ports 28A–28N permit sample to be introduced to eight columns (provided in channels 45A–45N); a slurry inlet port 26 is used during a column packing procedure to admit slurry to the device 10; and a fluidic port 30 that is used (1) during the packing process to exhaust (slurry) solvent from the device 10; and (2) during operation of the separation device 10 to exit mobile phase solvent and sample from the device 10 following separation. The first through sixth layers 11–16 each define eight optical detection windows 32A–32N. Defining these windows 32A–32N through these layers 11–16 facilitates optical detection since it reduces the amount of material between an optical detector (not shown) such as a conventional UV-VIS detector, and the samples contained in output channel segments 70A–70N downstream of the column-containing channels 45.

The second through seventh layers 12–17 define solvent vias 22A to transport a first mobile phase channel 64 defined in the eighth layer 18, with further solvent vias 24A defined in the second through fifth layers 12–15 to transport a second mobile phase solvent to the channel 46 defined in the sixth layer 16. Further vias 30A are defined in the second through sixth layers 12–16 to provide a fluid path between the fluidic port 30 and the channel 62 defined in the seventh layer 17. A via 26 defined in the second layer 12 communicates slurry from the slurry inlet port 26 to an elongate channel 38 defined in the third layer 13 during the slurry packing process. Preferably, particulate material deposited by the slurry packing process fills the channel 42 and at least a portion of the channel 38. The second layer 12 further defines eight sample channels 35A–35N having enlarged regions 34A–34N aligned with the sample inlet ports 28 defined in the first layer 11.

The third layer 13 defines an elongate channel 38 along with eight sample vias 36 aligned with the ends of the sample channels 35. The fourth channel defines eight sample vias 44 aligned with the vias 36 in the third channel 13. A (sample) frit 40 is placed between the third and fourth layers 13, 14. Although various frit materials may be used, the frit 40 (along with frits 50, 51) is preferably constructed from a permeable polypropylene membrane such as, for example, 1-mil (25 micron) thickness Celgard 2500 membrane (55% porosity, 0.209×0.054 micron pore size, Celgard Inc., Charlotte, N.C.), particularly if the layers 11–19 of the device 10 are bonded together using an adhesiveless thermal bonding method utilizing platens, such as described above. Applicants have obtained favorable results using this specific frit material, without noticeable wicking or lateral flow within the frit despite using a single strip of the frit membrane to serve multiple adjacent column-containing channels. As an alternative to the single frit 40, multiple discrete frits (not shown) of various porous material types and thickness may be substituted. The fourth layer 14 further defines a manifold channel 42 that provides fluid communication with the separation channels 45A–45N defined in the fifth layer 15 and the elongate channel 38 defined in the third layer 13. The separation channels 45A–45N are preferably about 40 mils (1 mm) wide or smaller.

The sixth layer 46 defines a channel 46 that receives a second mobile phase solvent for transport to the slit 52 defined in the seventh layer 17, which facilitates mixing of the two solvents in the channel 64 downstream of the slit 52. Further defined in the sixth layer 16 are a first set of eight vias 48 for admitting mixed mobile phase solvent to the upstream end of the channels 45 and the separation columns contained therein, and a second set of eight vias 49 at the downstream end of the same channels 45 for receiving mobile phase solvent and sample. Two frits 50, 51 are placed between the sixth and the seventh layers 16, 17. The first (mobile phase solvent) frit 50 is placed immediately above the first set of eight vias 48, while the second (mobile phase+sample) frit 51 is placed immediately above the second set of eight vias 49 and below a similar set of eight vias 60 defined in the seventh layer 17. The seventh layer 17 defines a channel segment 58, two medium forked channel segments 68, and eight vias 54 for communicating mobile phase solvent through the frit 50 and the vias 48 to the separation columns contained in the channels 45A–45N defined in the fifth layer 15. The seventh layer 17 further defines a transverse manifold channel 62 that receives mobile phase solvent and sample during separation, and that receives (slurry) solvent during column packing, for routing such fluids through vias 30A to the fluidic exit port 30. The eighth layer 18 defines a mixing channel 64, one large forked channel segment 68, and four small forked channel segments 66. The eighth layer 18 further defines eight parallel channel segments 70 downstream of the frit 51 for receiving (mobile phase) solvent and sample (during separation) or (slurry) solvent (during slurry packing), and for transporting such fluid(s) to the manifold channel 62 defined in the seventh layer 17. The ninth layer 19 serves as a cover for the channel structures defined in the eighth layer 18.

FIG. 6B is a top view of the assembled device 10 of FIG. 6A. FIGS. 6C–6D provide expanded views of two portions of the device 10. FIG. 6C shows the sample injection channels 35A–35N with associated enlarged regions 34A–34N that are aligned with the sample inlet ports 28A–28N defined in the first layer 11. For simplicity, the frit 40 has been omitted from FIG. 6C, although FIGS. 6A–6B correctly show the frit 40 placed between the sample vias 36, 44 upstream of the point where samples are injected onto the separation channels 45A–45N to be filled with particulate column material. FIG. 6D shows the mixing and splitting channel structures that communicate mobile phase solvent to the column-containing channels 45A–45N. During operation of the device 10, a first mobile phase solvent is injected into a first solvent inlet port 22 and flows into channel 64. A second mobile phase solvent is injected into a second solvent inlet port 24 and flows through the channel segment 46 through a slit 52 where it is layered with and joins the first solvent in the channel 64. The two layered solvents mix in the channel 64 and subsequent channel segment 58, whereafter the mixed solvent stream is split into eight portions or substreams by way of transport through a large forked channel segment 68, two medium forked channel segments 56, and four small forked channel segments 66. Alternatively, each solvent could be distributed by independent splitters (not shown). Also, the solvents could be mixed in a mixing chamber (not shown) before introduction into the separation channels 45A–45N or could be mixed in the separate channels. The eight solvent mixture substreams are then injected through vias 54 and 48 into the (column-containing) separation channels 45A–45N. For simplicity, the frit 50 disposed between the vias 54 and 48 have been omitted in FIG. 6D, although this frit 50 is shown in FIGS. 6A–6B.

Preferably, the various layers 11–19 of the device 10 are fabricated from unoriented polypropylene and bonded using an adhesiveless thermal bonding method utilizing platens, as described above. This construction method yields chemically resistant devices having high bond strength, both desirable attributes for withstanding a column packing process and subsequent operation to provide separation utility.

While the device 10 illustrated in FIGS. 6A–6D represents a preferred fluidic device, a wide variety of other fluidic devices may be used. In certain embodiments, fluidic devices may include one or more tubes, particularly capillary tubes. For example, capillary tubes may be embedded in one or more channels of a microfluidic device.

In liquid chromatography applications, it is often desirable to alter the makeup of the mobile phase during a particular separation. If multiple separation columns are provided in a single integrated device (such as the device 10) and the makeup of the mobile phase is subject to change over time, then at a common linear distance from the mobile phase inlet it is desirable for mobile phase to have a substantially identical composition from one column to the next. This is achieved with the device 10 due to two factors: (1) volume of the path of each (split) mobile phase solvent substream (shown in FIG. 6D) is substantially the same to each column; and (2) each flow path downstream of the fluidic (mobile phase and sample) inlets is characterized by substantially the same impedance.

The first factor, substantially equal substream flow paths, is promoted by design of the multi-splitter incorporating elements 58, 68, 56, and 66. The second factor, substantial equality of the impedance of each column, is promoted by both design of the fluidic device 10 and the fabrication of multiple columns in fluid communication (e.g., having a common outlet) using a slurry packing method. Where multiple columns are in fluid communication with a common outlet, slurry flow within the device is biased toward any low impedance region. The more slurry that flows to a particular region during the packing process, the more particulate is deposited to locally elevate the impedance, thus yielding a self-correcting method for producing substantially equal impedance from one column to the next.

Thus, FIGS. 6A–6D illustrate a multi-layer device 10 having multiple functional features (separation channels 45A–45N, optical detection windows 32A–32N), independent inlets and outlets (sample inlet ports 28A–28N, outlet channel segments 70A–70N), and three distributing inputs (slurry inlet 26, solvent inputs 22, 24). As discussed above, a device having three or more functional features and/or three or more common inputs will necessarily have channel crossings. The term "channel crossing" as used herein refers to the crossing of any fluid carrying features of a device, including, but not limited to channels crossing channels, chambers crossing chambers, functional features crossing functional features, channels crossing chambers, channels crossing functional features and any other possible combination. Moreover, a device having three or more functional features and/or three or more common inputs, where common fluids must be divided and distributed accurately and evenly preferably has impedance-matched input channels, and more preferably achieves impedance-matching by means of input channels of substantially equal length—a state most efficiently achieved with no restriction on channel crossings or channel geometry relative to other channels or the overall device.

Thus, by necessity and preference, the device 10 includes numerous channel crossings 72A–72N. In the device 10, however, these channel crossings 72A–72N do not allow undesirable fluid communication between the channels that cross, because at least one device layer is disposed between the crossing channels at these channel crossings 72A–72N. For example, a splitter channel 68 in device layer 18 crosses a separation channel 45B in device layer 15 at channel crossing 77A. However, other device layers 16, 17 are disposed between the device layers 15, 18 in question, thereby preventing any undesirable fluid communication between splitter channel 68 and separation channel 45B at channel crossing 77A.

FIGS. 6A–6D also illustrate that distributing inputs need not distribute only samples, solvents, or reagents for the actual fluidic operation to be performed. Distributing inputs may be used to pre-treat, charge, load or otherwise provide structural or chemical elements of the functional feature—in the case of the device 10, a distributing input (i.e., slurry input 26 and the channel 38 and the manifold channel 42) distributes to each of the functional features (i.e., separation channels 45A–45N) a particulate-containing slurry that packs the separation channels 45A–45N with the particulate material. Once the separation channels 45A–45N are packed and the device is operated, the particulate matter effects the separation performed the device 10.

Referring to FIGS. 7A–7B, a microfluidic device 700 for combining fluids is provided. The device 700 may be used for performing assays, dilutions, reactions or any other operation where the combination of two or more fluids is desirable. The device 700 is constructed from eight device layers 702–709. The first device layer 702 is a substrate to support the device 700 and seal the microfluidic structures defined in the second device layer 703. The second device layer 703 defines a plurality of functional features 710A–710N, sample inputs 712A–712N, and outputs 714A–714N. The third layer defines input vias 716A, output vias 718B and a plurality of reagent vias 720A. The fourth device layer 705 defines input vias 716B, output vias 718B, a plurality of reagent vias 720B and a reagent splitter 724A.

The next three device layers 706–708 each define input vias 716C–716E, output vias 718C–718E, a plurality of reagent vias 720C–720N and reagent splitters 724B–724N. The last device layer 709 defines input ports 716N, output ports 718N and distributing inputs 722A–722N. The last device layer 709 also seals the device 700. The functional features 710A–710N may be mixers, reactors or any other structures in which it is desirable to combine fluids.

In operation, fluid samples are supplied to the device 700 through the input ports 715A–715N. The samples travel through the input vias 716B–716N and into the functional features 710A–710N. Reagents with which the samples are to be mixed are introduced at inputs 722A–722N, which travel through vias 720A–720N into the splitters 724A–724N and then into the functional features 710A–710N. It should be noted that the splitters 724A–724N are geometrically symmetrical, thereby insuring that any fluid introduced into each splitter 724A–724N will divide into four equal portions before being delivered to the mixing chambers 710A–710N.

The device 700 includes multiple functional features (functional features 710A–710N), independent inlets and outlets (input ports 715A–715N), and four distributing inputs (the combination of inputs 722A–722N, vias 720A–720N and splitters 724A–724N). Consequently, for the reasons described above, numerous channel crossings 740A–740N are apparent. However, because the device is constructed from multiple layers, the channels in question may be defined in non-adjacent layers, whereby any intervening layers prevent undesirable fluid communication between the crossing channels.

Moreover, it may be noted that all inputs 722A–722N, 715A–715N and outputs 717A–717N are positioned along two outer edges of the device 10. Because multiple device layers 702–709 are used to fabricate the device 10, channel crossings need not be avoided, thereby allowing the input and output ports to be positioned anywhere on the device 10 suitable to provide compatibility with other devices that might be used in conjunction with the device 10. In this embodiment, inputs 722A–722N, 715A–715N and outputs 717A–717N are positioned along two outer edges of the device 10; however, it will be apparent to one skilled in the art that any desirable positioning of inputs and outputs may be selected.

FIGS. 3A–3B, 4A–4B, 5A–5B, 6A–6D and 7A–7B illustrate several devices suitable for providing samples to multiple functional features to be combined with multiple reagents. It should be understood that such microfluidic devices may be modified to reduce or increase the number of samples and reagents that may be used, simply by increasing or decreasing the number of chambers, inputs, splitters and device layers.

It is to be understood that the illustrations and descriptions of views of individual microfluidic tools, devices, and methods provided herein are intended to disclose components that may be combined in a working device. Various arrangements and combinations of individual tools, devices, and methods provided herein are contemplated, depending on the requirements of the particular application. The particular microfluidic tools, devices, and methods illustrated and described herein are provided by way of example only, and are not intended to limit the scope of the invention.

What is claimed is:

1. A multi-layer microfluidic device comprising a plurality of device layers, the plurality of device layers defining:
   at least three functional features;
   a first, a second, and a third distributing input each associated with each of the at least three functional features; and
   a channel crossover region that includes:
      a first distribution channel of the first distributing input, the first distribution channel defined in a first device layer of the plurality of device layers;
      a second distribution channel of the second distributing input, the second distribution channel defined in a second device layer of the plurality of device layers; and
      a third device layer of the plurality of device layers disposed between the first device layer and the second device layer, wherein the third device layer prevents fluid communication between the first distribution channel and the second distribution channel at the channel crossover region.

2. The multi-layer microfluidic device of claim 1 wherein:
   each distributing input defines a fluid flow path to each functional feature of the at least three functional features;
   each fluid flow path has a characteristic impedance to fluid flow; and
   the impedances of the fluid flow paths are substantially equal.

3. The multi-layer microfluidic device of claim 1 wherein:
   each distributing input defines a fluid flow path to each functional feature of the at least three functional features;
   each fluid flow path has a characteristic length; and
   the lengths of the fluid flow paths are substantially equal.

4. The multi-layer microfluidic device of claim 1 wherein the plurality of device layers further defines a plurality of fluidic outputs each being in fluid communication with at least one functional feature of the at least three functional features.

5. The multi-layer microfluidic device of claim 1, wherein the plurality of device layers further defines a plurality of independent fluidic inputs each being in fluid communication with at least one functional feature of the at least three functional features.

6. The multi-layer microfluidic device of claim 1 wherein at least one device layer of the plurality of device layers is a stencil layer.

7. The multi-layer microfluidic device of claim 1 wherein any device layer of the plurality of device layers is fabricated with a polymeric material.

8. The multi-layer microfluidic device of claim 1 wherein any device layer of the plurality of device layers is fabricated with a self-adhesive tape material.

9. The multi-layer microfluidic device of claim 1 wherein the at least three functional features are selected from the group consisting of: mixers, separation channels, reaction chambers, and analysis windows.

10. A multi-layer microfluidic device comprising:
    at least three functional features;
    at least three distributing inputs each including a plurality of channels, each distributing input being in fluid communication with the at least three functional features;
    a plurality of channel crossings; and
    an intervening device layer preventing fluid communication between any of the at least three distributing inputs at any channel crossing of the plurality of channel crossings.

11. The multi-layer microfluidic device of claim 10 wherein:
    at least one distributing input defines a fluid flow path to each of the at least three functional features;

each fluid flow path has a characteristic fluidic impedance; and the fluidic impedances of the fluid flow paths are substantially equal.

12. The multi-layer microfluidic device of claim 10 wherein:

at least one distributing input defines a fluid flow path to each of the at least three functional features;

each fluid flow path has a characteristic length; and the lengths of the fluid flow paths are substantially equal.

13. The multi-layer microfluidic device of claim 10, further comprising a plurality of fluidic outputs each being in fluid communication with at least one functional feature of the at least three functional features.

14. The multi-layer microfluidic device of claim 10, further comprising a plurality of independent fluidic inputs each being in fluid communication with at least one functional feature of the at least three functional features.

15. The multi-layer microfluidic device of claim 10 wherein the device is fabricated with a plurality of device layers, and at least one device layer of the plurality of device layers is a stencil layer.

16. The multi-layer microfluidic device of claim 10 wherein the device is fabricated with a plurality of device layers, and any device layer of the plurality of device layers is fabricated with a polymeric material.

17. The multi-layer microfluidic device of claim 10 wherein the device is fabricated with a plurality of device layers, and any device layer of the plurality of device layers is fabricated with a self-adhesive tape material.

18. The multi-layer microfluidic device of claim 10 wherein the at least three functional features are selected from the group consisting of: mixers, separation channels, reaction chambers, and analysis windows.

19. A multi-layer microfluidic device comprising:

a functional device layer defining at least three functional features;

a first device layer having a first set of distribution channels in fluid communication with the at least three functional features;

a second device layer having a second set of distribution channels in fluid communication with the at least three functional features; and a third device layer having a third set of distribution channels in fluid communication with the at least three functional features;

wherein the second device layer is disposed between the first device layer and the third device layer.

20. The multi-layer microfluidic device of claim 19 wherein:

any of the first, second, and third set of distribution channels defines a plurality of fluid flow paths;

at least three fluid flow paths of the plurality of fluid flow paths has a characteristic fluidic impedance; and the fluidic impedances of the at least three fluid flow paths are substantially equal.

21. The multi-layer microfluidic device of claim 19 wherein:

any of the first, second, and third set of distribution channels defines a plurality of fluid flow paths;

at least three fluid flow paths of the plurality of fluid flow paths has a characteristic length; and the lengths of the at least three fluid flow paths are substantially equal.

22. The multi-layer microfluidic device of claim 19 wherein any of the functional device layer, the first device layer, the second device layer, and the third device layer includes a plurality of sublayers.

23. The multi-layer microfluidic device of claim 22 wherein the plurality of sublayers includes a stencil layer.

24. The multi-layer microfluidic device of claim 19 wherein any of the functional device layer, the first device layer, the second device layer, and the third device layer is a stencil layer.

25. The multi-layer microfluidic device of claim 19 wherein any of the functional device layer, the first device layer, the second device layer, and the third device layer is fabricated with a polymeric material.

26. The multi-layer microfluidic device of claim 19 wherein any of the functional device layer, the first device layer, the second device layer, and the third device layer is fabricated with a self-adhesive tape material.

27. The multi-layer microfluidic device of claim 19 wherein the at least three functional features are selected from the group consisting of: mixers, separation channels, reaction chambers, and analysis windows.

28. A multi-layer microfluidic device comprising:

a first device layer defining at least three functional features and a first distributing input in fluid communication with each of the at least three functional features;

a second device layer defining a second distributing input in fluid communication with each of the at least three functional features;

a third distributing input defined in one of the first device layer or the second device layer, the third distributing input being in fluid communication with each of the at least three functional features; and a third device layer disposed between the first device layer and the second device layer.

29. The multi-layer microfluidic device of claim 28 wherein any of the first distributing input, the second distributing input, and the third distributing input defines a plurality of fluid flow paths, and at least three fluid flow paths of the plurality of fluid flow paths are substantially impedance-matched.

30. The multi-layer microfluidic device of claim 28 wherein any of the first distributing input, the second distributing input, and the third distributing input defines a plurality of fluid flow paths each having a length, and at least three fluid flow paths of the plurality of fluid flow paths have substantially the same length.

31. The multi-layer microfluidic device of claim 28 wherein any of the first device layer, the second device layer, and the third device layer includes a plurality of sublayers.

32. The multi-layer microfluidic device of claim 28 wherein the plurality of sublayers includes a stencil layer.

33. The multi-layer microfluidic device of claim 28 wherein any of the first device layer, the second device layer, and the third device layer is a stencil layer.

34. The multi-layer microfluidic device of claim 28 wherein any of the first device layer, the second device layer, and the third device layer is fabricated with a polymeric material.

35. The multi-layer microfluidic device of claim 28 wherein any of the first device layer, the second device layer, and the third device layer is fabricated with a self-adhesive tape material.

36. The multi-layer microfluidic device of claim 28 wherein the at least three functional features are selected from the group consisting of: mixers, separation channels, reaction chambers, and analysis windows.

* * * * *